(12) United States Patent
Sugi et al.

(10) Patent No.: US 8,017,378 B2
(45) Date of Patent: Sep. 13, 2011

(54) METHOD FOR PRODUCTION OF OPTICALLY ACTIVE BIPHENYLALANINE COMPOUND OR SALT OR ESTER THEREOF

(75) Inventors: Kiyoshi Sugi, Osaka (JP); Masahide Tanaka, Hyogo (JP); Yoshihiro Kawada, Osaka (JP); Daisuke Sasayama, Osaka (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 616 days.

(21) Appl. No.: 12/087,753

(22) PCT Filed: Jan. 15, 2007

(86) PCT No.: PCT/JP2007/050851
§ 371 (c)(1),
(2), (4) Date: Jul. 14, 2008

(87) PCT Pub. No.: WO2007/083776
PCT Pub. Date: Jul. 26, 2007

(65) Prior Publication Data
US 2009/0011475 A1    Jan. 8, 2009

(30) Foreign Application Priority Data
Jan. 17, 2006    (JP) ................................ 2006-009002

(51) Int. Cl.
C12P 41/00    (2006.01)
(52) U.S. Cl. ...................................................... 435/280
(58) Field of Classification Search ........................ None
See application file for complete search history.

(56) References Cited

U.S. PATENT DOCUMENTS

| 4,262,092 A | 4/1981 | Bauer |
| 5,294,632 A | 3/1994 | Erion et al. |

FOREIGN PATENT DOCUMENTS

| JP | 6-228187 A | 8/1994 |
| JP | 09-206089 | 8/1997 |
| JP | 2003-261522 | 9/2003 |
| WO | WO 2004/055195 A1 | 7/2004 |

OTHER PUBLICATIONS

Notification of the First Office Action of the corresponding Chinese Patent Application No. 200780002319.6, dated Feb. 12, 2010.
Office Action of the corresponding Chinese Patent Application No. 200780002319.6, dated Feb. 12, 2010.
Miyazawa, T., "Enzymatic resolution of amino acids via ester hydrolysis", *Amino Acids*, 1999, vol. 16, pp. 191-213.
Kijima, Tatsuro, et al., "Facile Optical Resolution of Amino Acid Esters via Hydrolysis by an Industrial Enzyme in Organic Solvents", J. Chem. Tech. Biotechnol., 1994, 59, pp. 61-65.
Kijima, Tatsuro, et al., "Facile Synthesis of L-DOPA (3,4-Dihydroxyphenylalanine) Which is an Effective Medicine for the Treatment of Parkinson's Disease by Alkaline Protease in Organic Solvents", ITE Letters on Batteries, New Technologies & Medicines, vol. 5, No. 4, 2004, pp. 377, 379, 380.
Zhao, Hua, et al., "Concise Synthesis and Enzymatic Resolution of L-(+)-Homophenylalanine Hydrochloride", Enantiomer, vol. 7, 2002, pp. 1-3.
Chen, Shui-Tein, et al., "Resolution of Amino Acids in a Mixture of 2-Methyl-2-propanol/Water (19:1) Catalyzed by Alcalase via in Situ Racemization of One Antipode Mediated by Pyridoxal 5-Phosphate", J. Org. Chem., 59, 1994, pp. 7580-7581.
Supplementary Search Report mailed Sep. 16, 2009, received in European Application No. 07713656.2.
Kise, Hideo et al., "Unusual Solvent Effect on Protease Activity and Effective Optical Resolution of Amino Acids by Hydrolytic Reactions in Organic Solvents," Biotechnology Letters, vol. 13, No. 5, 1991, pp. 317-322.
Firooznia, Fariborz et al., "Enantioselective Synthesis of 4-Substituted Phenylalanines by Cross-Coupling Reactions," Tetrahedron Letters, vol. 40, 1999, pp. 213-216.

*Primary Examiner* — Sandra Saucier
(74) *Attorney, Agent, or Firm* — Foley & Lardner LLP

(57) ABSTRACT

Disclosed is a method for production of an optically active biphenylalanine compound represented by the formula (2):

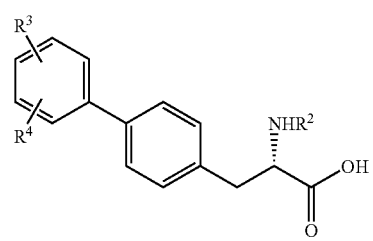

(2)

(wherein, $R^2$ is a protective group of an amino group, and $R^3$ and $R^4$ are each independently a hydrogen atom, etc.) or a salt thereof and an optically active biphenylalanine ester compound represented by the formula (3):

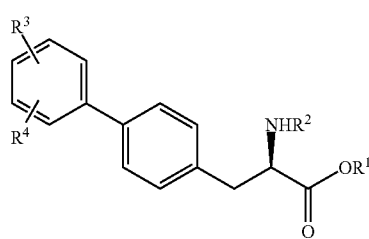

(3)

(wherein, $R^1$ is an alkyl group, etc.)
wherein the method comprises hydrolyzing a biphenylalanine ester compound represented by the formula (1):

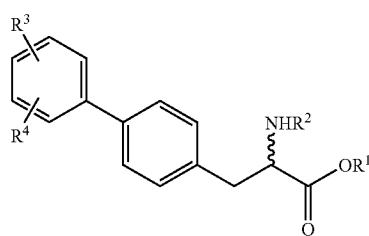

(1)

with a protease produced by a microorganism belonging to *Bacillus* sp. in the presence of at least one alkali selected from an alkali metal hydroxide and an alkaline earth metal hydroxide.

23 Claims, No Drawings

METHOD FOR PRODUCTION OF OPTICALLY ACTIVE BIPHENYLALANINE COMPOUND OR SALT OR ESTER THEREOF

TECHNICAL FIELD

The present invention relates to a method for producing a compound having an optically active biphenylalanine structure useful as an intermediate of medicaments or the like.

BACKGROUND ART

A compound having an optically active biphenylalanine structure is useful as an intermediate of medicaments such as a neutral endopeptidase inhibitor (cf. JP-H06-228187A and JP-2003-261522A).

The known methods for producing optically active biphenylalanine compounds are (1) a method including the steps of changing D-Boc-tyrosine methyl ester into triflate, subjecting the triflate to Suzuki coupling, and hydrolyzing the obtained ester (cf. U.S. Pat. No. 5,217,996) and (2) a method for synthesizing optically active Boc-biphenylalanine by asymmetric hydrogenation (cf. Chirality, 1996, Vol. 8, No. 2, p. 173-188 and JP-2003-261522A). However, as for the method (1), followings are known, that is, a reagent for making triflate is expensive, palladium as a catalyst used for Suzuki coupling is expensive, it is hard to remove residual palladium from a product, and D-tyrosine used as a raw material to make D-biphenylalanine is expensive. Therefore, the method (1) is not industrially effective. Further, the method (2) has a problem wherein a catalyst and an asymmetric source which are used for asymmetric hydrogenation are expensive.

On the other hand, as for a method for producing an optically active amino acid derivative, it is known to asymmetrically hydrolyze a racemate of N-(2,6-dimethylphenyl) alanine ester by using an enzyme (cf. WO2004/055195A). In addition, it is also known to produce an optically active amino acid or an optically active phenylalanine derivative by asymmetric hydrolysis using enzyme (cf. J. Chem. Technol. Biotechnol., 1994, Vol. 59, p. 61-65; ITE Letters on Batteries, New Technologies & Medicine, 2004, Vol. 5, No. 4, p. 377-380 ITE-Hohwa Inc.; Enantiomer, 2002, Vol. 7, No. 1, p. 1-3; Biotechnol. Lett., 1991, Vol. 13, No. 5, p. 317-322; and ES-547913A).

Further, it is known that N-substituted-L-amino acid and N-substituted-D-amino acid ester are produced by hydrolysis of racemic N-substituted-DL-amino acid ester by using protease in the presence of a weak base as a pH controlling reagent (cf. JP-H09-206089A).

DISCLOSURE OF THE INVENTION

An object of the present invention is to provide a method for producing a compound having an optically active biphenylalanine structure with high optical purity, low cost, and an easy operation without giving much load to environment.

This object and other objects are obtained by the following descriptions.

Present inventors worked to solve the above-described problems and, as a result, they found out the present invention.

That is, the present invention is as follows.

[1] A method for producing an optically active biphenylalanine compound represented by the formula (2) (hereinafter, it may be called as an optically active biphenylalanine compound (2)):

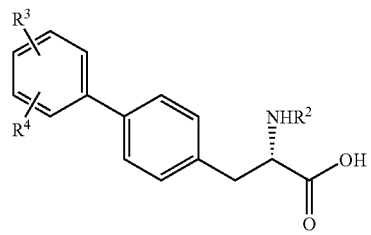

(wherein, $R^2$ is a protective group of an amino group, and $R^3$ and $R^4$ are each independently a hydrogen atom, a halogen atom, an alkyl group, a haloalkyl group, a hydroxy group, an alkoxy group, a cyano group or a nitro group)

or a salt thereof and an optically active biphenylalanine ester compound represented by the formula (3) (hereinafter, it may be called as an optically active biphenylalanine ester compound (3)):

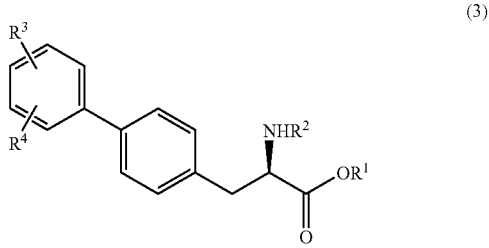

(wherein, $R^1$ is an alkyl group, a haloalkyl group, an alkenyl group, a cycloalkyl group, an aryl group being optionally substituted, or an aralkyl group being optionally substituted; and $R^2$, $R^3$ and $R^4$ have the same meanings as described above) which comprises the step of hydrolyzing a biphenylalanine ester compound represented by the formula (1) (it may be called as a biphenylalanine ester compound (1) below):

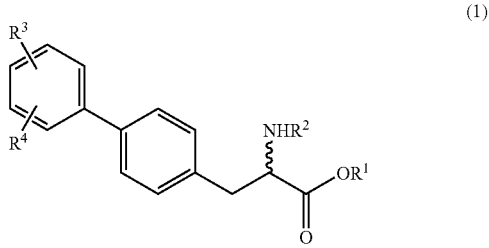

(wherein, $R^1$, $R^2$, $R^3$ and $R^4$ have the same meanings as described above)

with protease produced by a microorganism belonging to Bacillus sp. in the presence of at least one alkali selected from an alkali metal hydroxide and an alkaline earth metal hydroxide.

[2] The method described in the above [1], wherein the hydrolysis is carried out in the presence of an amino acid and at least one alkali selected from an alkali metal hydroxide and an alkaline earth metal hydroxide.

[3] The method described in the above [1], wherein the hydrolysis is carried out in the presence of an aminosulfonic acid and at least one alkali selected from an alkali metal hydroxide and an alkaline earth metal hydroxide.

[4] The method described in any one of the above [1] to [3], wherein the method further comprises the step of separating the optically active biphenylalanine compound represented by the formula (2) or a salt thereof from an optically active biphenylalanine ester compound represented by the formula (3) after the hydrolysis.

[5] The method described in any one of the above [1] to [4], wherein the alkali is an alkali metal hydroxide.

[6] The method described in any one of the above [2], [4] and [5], wherein the amino acid is glycine.

[7] The method described in any one of the above [3] to [5], wherein the aminosulfonic acid is taurine.

[8] The method described in above [2], wherein the alkali is an alkali metal hydroxide.

[9] The method described in above [6], wherein the alkali is an alkali metal hydroxide.

[10] The method described in above [3], wherein the alkali is an alkali metal hydroxide.

[11] The method described in above [7], wherein the alkali is an alkali metal hydroxide.

[12] The method described in any one of the above [1] to [11], wherein the protease is produced by *Bacillus licheniformis*.

[13] The method described in any one of the above [1] to [12], wherein $R^1$ is an alkyl group.

[14] The method described in any one of the above [1] to [13], wherein $R^1$ is a methyl group or an ethyl group.

[15] The method described in any one of the above [1] to [14], wherein $R^2$ is a tert-butoxycarbonyl group.

[16] The method described in any one of the above [1] to [15], wherein $R^3$ and $R^4$ are hydrogen atoms.

[17] The method described in any one of the above [1] to [16], wherein the hydrolysis is carried out while keeping the pH range of 6 to 13.

[18] The method described in any one of the above [1] to [16], wherein the hydrolysis is carried out while keeping the pH range of 6 to 10.

[19] The method described in any one of the above [1] to [18], wherein the hydrolysis is carried out in a mixed solvent of an organic solvent and water.

[20] The method described in above [19], wherein the organic solvent is at least one selected from tert-butyl methyl ether and toluene.

[21] The method described in above [20], wherein the organic solvent is tert-butyl methyl ether.

[22] The method described in any one of the above [1] to [21], wherein the hydrolysis is carried out at 30 to 60° C.

[23] The method described in any one of the above [1] to [21], wherein the hydrolysis is carried out at 35 to 55° C.

[24] A method for producing a biphenylalanine ester compound (1) which comprises a step for esterifying an optically active biphenylalanine compound (2) or a salt thereof so as to obtain an optically active biphenylalanine ester compound represented by the formula (2') (it may be called as an optically active biphenylalanine ester compound (2')):

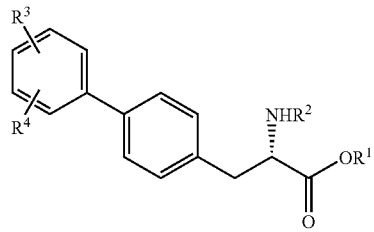

(2')

(wherein, $R^1$, $R^2$, $R^3$ and $R^4$ have the same meanings as described above) and a step for racemizing the optically active biphenylalanine ester compound (2') so as to obtain a biphenylalanine ester compound (1).

[25] A method for recovering a biphenylalanine ester compound (1) which comprises;
a step for separating the optically active biphenylalanine compound (2) or a salt thereof from a mixture containing an optically active biphenylalanine compound (2) or a salt thereof and an optically active biphenylalanine ester compound (3); a step for esterifying the optically active biphenylalanine compound (2) or salt thereof so as to obtain an optically active biphenylalanine ester compound (2'); and a step for racemizing the optically active biphenylalanine ester compound (2') so as to obtain the biphenylalanine ester compound (1).

BEST MODE FOR CARRYING OUT THE INVENTION

The definition of substituents used in this specification will be described below.

Examples of "alkyl group" include a C1-6 straight chain or branched chain alkyl group. Typical examples are a methyl group, an ethyl group, a propyl group, an isopropyl group, a butyl group, an isobutyl group, a sec-butyl group, a tert-butyl group, a pentyl group, an isopentyl group, a neopentyl group and a hexyl group. A methyl group and an ethyl group are preferable.

Examples of "alkenyl group" include a C2-6 straight chain or branched chain alkenyl group. Typical examples are a vinyl group, an alkyl group, a 1-propenyl group, an isopropenyl group, a 1-butenyl group, a 2-butenyl group and a 3-butenyl group. A vinyl group and an alkyl group are preferable.

Examples of "cycloalkyl group" include a C3-8 cycloalkyl group. Typical examples are a cyclopropyl group, a cyclobutyl group, a cyclopentyl group, a cyclohexyl group, a cycloheptyl group and a cyclooctyl group. A cyclopentyl group and a cyclohexyl group are preferable.

Examples of "halogen atom" include a fluorine atom, a chlorine atom, a bromine atom and an iodine atom. A fluorine atom, a chlorine atom and a bromine atom are preferable.

"Haloalkyl group" is the above-defined "alkyl group" substituted by the above-defined "halogen atom". The number of substitution by the halogen atom is not limited, but is preferably 1 to 3. Examples of "haloalkyl group" include a chloromethyl group, a bromomethyl group, a fluoromethyl group, a dichloromethyl group, a dibromomethyl group, a difluoromethyl group, a trichloromethyl group, a tribromomethyl group, a trifluoromethyl group, a 2,2-dichloromethyl group and a 2,2,2-trichloroethyl group. A trifluoromethyl group is preferable.

Examples of "alkoxy group" include a C1-6 straight chain or branched chain alkoxy group. Typical examples are a methoxy group, an ethoxy group, a propoxy group, an isopropoxy group, a butoxy group, an isobutoxy group, a sec-butoxy group, a tert-butoxy group, a pentyloxy group, an isopentyloxy group, a neopentyloxy group and a hexyloxy group. A methoxy group and an ethoxy group are preferable.

Examples of "aryl group" in "aryl group being optionally substituted" include a C6-14 aryl group. Typical examples are a phenyl group, a 1-naphthyl group and a 2-naphthyl group. A phenyl group is preferable.

The aryl group can have a substituent at its substitutable position, and examples of such a substituent are a halogen atom (which is the same as that defined above), an alkyl group (which is the same as that defined above), a haloalkyl group (which is the same as that defined above), a hydroxyl group, an alkoxy group (which is the same as that defined above), a cyano group and a nitro group. The number of the substituent is not limited, but is preferably 1 to 3. When the number of a substituent is 2 or more, these substituents can be the same or different.

"Aralkyl group" in "aralkyl group being optionally substituted" is the above-defined "alkyl group" substituted by the above-defined "aryl group". The number of substitution by the aryl group is not limited, but is preferably 1 to 3. Examples of "aralkyl group" include a benzyl group, a phenetyl group, a 1-phenylethyl group, a 1-phenylpropyl group, a 2-phenylpropyl group, a 3-phenylpropyl group, a 1-naphthylmethyl group, a 2-naphthylmethyl group, a benzhydryl group and a trityl group. A benzyl group is preferable.

The aralkyl group can have a substituent at its substitutable position, and examples of such a substituent are a halogen atom (which is the same as that defined above), an alkyl group (which is the same as that defined above), a haloalkyl group (which is the same as that defined above), a hydroxy group, an alkoxy group (which is the same as that defined above), a cyano group and a nitro group. The number of the substituent is not limited, but is preferably 1 to 3. When the number of a substituent is 2 or more, these substituents can be the same or different.

As "a protective group of an amino group" indicated with $R^2$, a publicly known protective group used as a protective group of an amino group can be used without any restriction. Examples of such a protective group include —$CO_2R^5$ (where, $R^5$ is an alkyl group, a haloalkyl group, an alkenyl group, an aryl group being optionally substituted, an aralkyl group being optionally substituted, or a 9-fluorenylmethyl group), —$COR^6$ (where, $R^6$ is a hydrogen atom, an alkyl group, a haloalkyl group, an alkenyl group, an aryl group being optionally substituted, or an aralkyl group being optionally substituted), and an aralkyl group being optionally substituted. Typical examples of "the protective group of an amino group" are a methoxycarbonyl group, an ethoxycarbonyl group, an isobutoxycarbonyl group, a tert-butoxycarbonyl group, an allyloxycarbonyl group, a benzyloxycarbonyl group, a p-methoxybenzyloxycarbonyl group, a p-nitrobenzyloxycarbonyl group, a 9-fluorenylmethyloxycarbonyl group, a formyl group, an acetyl group, a benzoyl group, a benzyl group, a benzhydryl group and a trityl group.

$R^1$ is preferably an alkyl group, and more preferably a methyl group and an ethyl group.

$R^2$ is preferably —$CO_2R^5$ (where, $R^5$ is the same as that defined above), and more preferably a tert-butoxycarbonyl group.

Both $R^3$ and $R^4$ are preferably hydrogen atoms.

For example, the biphenylalanine ester compound (1) as a raw material used in the method of the present invention can be produced by the following method.

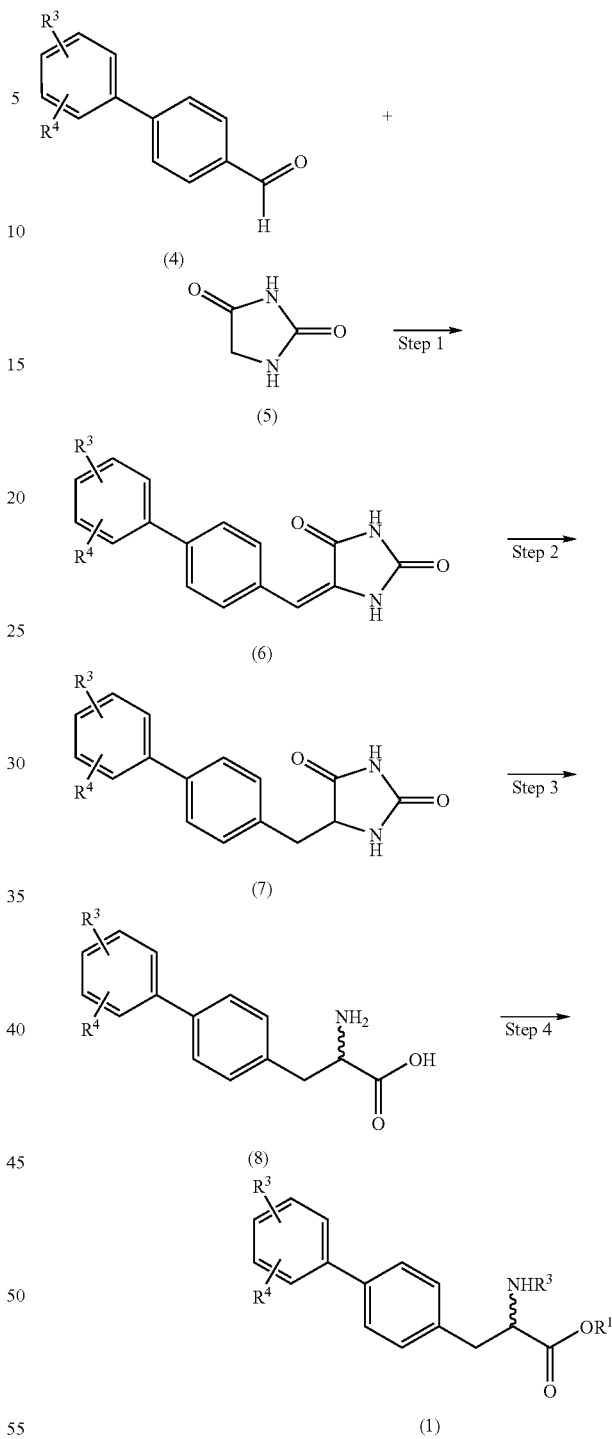

(wherein, $R^2$, $R^3$ and $R^4$ are the same as those defined above)

Step 1

A compound (6) can be obtained by a reaction of a compound (4) with hydantoin (5) in the presence of a base.

The amount of the hydantoin (5) is usually 1 to 3 moles, and preferably 1.05 to 2 moles based on 1 mole of the compound (4).

Examples of the base include ammonium acetate, sodium acetate, piperidine and triethylamine.

The amount of the base is usually 0.1 to 10 moles, and preferably 0.5 to 2 moles based on 1 mole of the compound (4).

Examples of the reaction solvent include acetic acid, acetic anhydride and N,N-dimethylformamide.

The reaction temperature is usually 30 to 200° C., and preferably 100 to 200° C. The reaction time is usually 1 to 24 hours, and preferably 3 to 10 hours.

Step 2

A compound (7) can be obtained by reducing a compound (6).

The reduction can be preferably carried out by catalytic hydrogenation.

Examples of the catalyst used in the catalytic hydrogenation include palladium-carbon, palladium hydroxide-carbon, platinum-carbon, rhodium-carbon, ruthenium-carbon and developed nickel.

When noble metals such as Pd is used, the amount of the catalyst is usually 0.0005 to 0.05 g, and preferably 0.005 to 0.02 g expressed in terms of metal amounts based on 1 g of the compound (6). When developed nickel is used, the amount is usually 0.1 to 2 g, and preferably 0.2 to 1 g.

Examples of the reaction solvent include ethers such as tetrahydrofuran, tert-butyl methyl ether, 1,2-dimethoxyethane and 1,4-dioxane; alcohols such as methanol, ethanol, isopropanol, n-butanol and tert-butanol; esters such as ethyl acetate, methyl acetate and butyl acetate; organic acids such as acetic acid and propionic acid; water; and mixtures thereof.

The catalytic hydrogenation can be carried out at atmospheric pressure or under pressure.

The reaction temperature is usually 20 to 100° C., and preferably 40 to 70° C. The reaction time is usually 1 to 24 hours, and preferably 3 to 10 hours.

Step 3

A compound (8) can be obtained by hydrolysis of a compound (7).

The hydrolysis can be generally carried out by treating the compound with a base in a solvent.

Examples of the base include sodium hydroxide, potassium hydroxide, lithium hydroxide, calcium hydroxide, barium hydroxide, potassium carbonate and sodium carbonate.

The amount of the base is usually 2 to 10 moles, and preferably 3 to 8 moles based on 1 mole of the compound (7).

Examples of the reaction solvent include alcohols such as methanol, ethanol and ethylene glycol; ethers such as tetrahydrofuran, tert-butyl methyl ether, 1,2-dimethoxyethane and 1,4-dioxane; water; and mixtures thereof.

The reaction temperature is usually 80 to 200° C., and preferably 100 to 170° C. The reaction time is usually 1 to 24 hours, and preferably 3 to 10 hours.

Step 4

A biphenylalanine ester compound (1) can be obtained by protecting an amino group in a compound (8) and esterifying a carboxyl group in the compound (8). Protection of the amino group and esterification of the carboxyl group can be carried out by ordinary methods. The order of protection of the amino group and esterification of the carboxyl group is not limited, and can be arbitrary.

The biphenylalanine ester compound (1) includes two optical isomers (L-form and D-form) based on the asymmetric center on the carbon atom at the α-position. However, the biphenylalanine ester compound (1) used in the method of the present invention can be a racemate including equivalent amounts of these optical isomers, or can be a mixture in which the amount of one optical isomer is excessive (in an arbitrary ratio). The racemate is preferable.

Examples of the biphenylalanine ester compound (1) include N-(tert-butoxycarbonyl) biphenylalanine methyl ester, N-(tert-butoxycarbonyl)biphenylalanine ethyl ester, N-(benzyloxycarbonyl)biphenylalanine methyl ester, N-(benzyloxycarbonyl)biphenylalanine ethyl ester, N-(tert-butoxycarbonyl)-4'-methylbiphenylalanine methyl ester, N-(tert-butoxycarbonyl)-4'-methylbiphenylalanine ethyl ester, N-(benzyloxycarbonyl)-4'-methylbiphenylalanine methyl ester, N-(benzyloxycarbonyl)-4'-methylbiphenylalanine ethyl ester, N-(tert-butoxycarbonyl)-3'-methylbiphenylalanine methyl ester, N-(tert-butoxycarbonyl)-3'-methylbiphenylalanine ethyl ester, N-(benzyloxycarbonyl)-3'-methylbiphenylalanine methyl ester, N-(benzyloxycarbonyl)-3'-methylbiphenylalanine ethyl ester, N-(tert-butoxycarbonyl)-2'-methylbiphenylalanine methyl ester, N-(tert-butoxycarbonyl)-2'-methylbiphenylalanine ethyl ester, N-(benzyloxycarbonyl)-2'-methylbiphenylalanine methyl ester, N-(benzyloxycarbonyl)-2'-methylbiphenylalanine ethyl ester, N-(tert-butoxycarbonyl)-4'-ethylbiphenylalanine methyl ester, N-(tert-butoxycarbonyl)-4'-ethylbiphenylalanine ethyl ester, N-(benzyloxycarbonyl)-4'-ethylbiphenylalanine methyl ester, N-(benzyloxycarbonyl)-4'-ethylbiphenylalanine ethyl ester, N-(tert-butoxycarbonyl)-4'-n-propylbiphenylalanine methyl ester, N-(tert-butoxycarbonyl)-4'-n-propylbiphenylalanine ethyl ester, N-(benzyloxycarbonyl)-4'-n-propylbiphenylalanine methyl ester, N-(benzyloxycarbonyl)-4'-n-propylbiphenylalanine ethyl ester, N-(tert-butoxycarbonyl)-2'-isopropylbiphenylalanine methyl ester, N-(tert-butoxycarbonyl)-2'-isopropylbiphenylalanine ethyl ester, N-(benzyloxycarbonyl)-2'-isopropylbiphenylalanine methyl ester, N-(benzyloxycarbonyl)-2'-isopropylbiphenylalanine ethyl ester, N-(tert-butoxycarbonyl)-3'-isopropylbiphenylalanine methyl ester, N-(tert-butoxycarbonyl)-3'-isopropylbiphenylalanine ethyl ester, N-(benzyloxycarbonyl)-3'-isopropylbiphenylalanine methyl ester, N-(benzyloxycarbonyl)-3'-isopropylbiphenylalanine ethyl ester, N-(tert-butoxycarbonyl)-4'-isopropylbiphenylalanine methyl ester, N-(tert-butoxycarbonyl)-4'-isopropylbiphenylalanine ethyl ester, N-(benzyloxycarbonyl)-4'-isopropylbiphenylalanine methyl ester, N-(benzyloxycarbonyl)-4'-isopropylbiphenylalanine ethyl ester, N-(tert-butoxycarbonyl)-4'-n-butylbiphenylalanine methyl ester, N-(tert-butoxycarbonyl)-4'-n-butylbiphenylalanine ethyl ester, N-(benzyloxycarbonyl)-4'-n-butylbiphenylalanine methyl ester, N-(benzyloxycarbonyl)-4'-n-butylbiphenylalanine ethyl ester, N-(tert-butoxycarbonyl)-4'-t-butylbiphenylalanine methyl ester, N-(tert-butoxycarbonyl)-4'-t-butylbiphenylalanine ethyl ester, N-(benzyloxycarbonyl)-4'-t-butylbiphenylalanine methyl ester, N-(benzyloxycarbonyl)-4'-t-butylbiphenylalanine ethyl ester, N-(tert-butoxycarbonyl)-3',5'-dimethylbiphenylalanine methyl ester, N-(tert-butoxycarbonyl)-3',5'-dimethylbiphenylalanine ethyl ester, N-(benzyloxycarbonyl)-3',5'-dimethylbiphenylalanine methyl ester, N-(benzyloxycarbonyl)-3',5'-dimethylbiphenylalanine ethyl ester, N-(tert-butoxycarbonyl)-3',4'-dimethylbiphenylalanine methyl ester, N-(tert-butoxycarbonyl)-3',4'-dimethylbiphenylalanine ethyl ester, N-(benzyloxycarbonyl)-3',4'-dimethylbiphenylalanine methyl ester, N-(benzyloxycarbonyl)-3',4'-dimethylbiphenylalanine ethyl ester, N-(tert-butoxycarbonyl)-2'-methoxy-5'-methylbiphenylalanine methyl ester, N-(tert-butoxycarbonyl)-2'-methoxy-5'-methylbiphenylalanine ethyl ester, N-(benzyloxycarbonyl)-2'-methoxy-5'-methylbiphenyl alanine methyl ester, N-(benzyloxycarbonyl)-2'-methoxy-5'-methylbiphenylalanine ethyl ester, N-(tert-butoxycarbonyl)-4'-methoxy-2'-methylbiphenylalanine methyl ester, N-(tert-butoxycarbonyl)-4'-methoxy-2'-methylbiphenylalanine ethyl ester, N-(benzyloxycarbonyl)-4'-methoxy-2'-methylbiphenylalanine methyl ester, N-(benzyloxycarbonyl)-4'-methoxy-2'-methylbiphenylalanine ethyl ester, N-(tert-butoxycarbonyl)-2'-methoxybiphenylalanine methyl ester, N-(tert-butoxycarbonyl)-2'-methoxybiphenylalanine ethyl ester, N-(benzyloxycarbonyl)-2'-methoxybiphenylalanine methyl ester, N-(benzyloxycarbonyl)-2'-methoxybiphenylalanine ethyl ester, N-(tert-butoxycarbonyl)-3'-methoxybiphenylalanine methyl ester, N-(tert-butoxycarbonyl)-3'-methoxybiphenylalanine ethyl ester, N-(benzyloxycarbonyl)-3'-methoxybiphenylalanine methyl ester, N-(benzyloxycarbonyl)-3'-methoxybiphenylalanine ethyl ester, N-(tert-butoxycarbonyl)-4'-methoxybiphenylalanine methyl ester, N-(tert-butoxycarbonyl)-4'-methoxybiphenylalanine ethyl ester, N-(benzyloxycarbonyl)-4'-methoxybiphenylalanine methyl ester, N-(benzyloxycarbonyl)-4'-methoxybiphenylalanine ethyl ester, N-(tert-butoxycarbonyl)-2'-benzyloxybiphenylalanine methyl ester, N-(tert-butoxycarbonyl)-2'-benzyloxybiphenylalanine ethyl ester, N-(benzyloxycarbonyl)-2'-benzyloxybiphenylalanine methyl ester, N-(benzyloxycarbonyl)-2'-benzyloxybiphenylalanine ethyl ester, N-(tert-butoxycarbonyl)-3'-benzyloxybiphenylalanine methyl ester, N-(tert-butoxycarbonyl)-3'-benzyloxybiphenylalanine ethyl ester, N-(benzyloxycarbonyl)-3'-benzyloxybiphenylalanine methyl ester, N-(benzyloxycarbonyl)-3'-benzyloxybiphenylalanine ethyl ester, N-(tert-butoxycarbonyl)-4'-benzyloxybiphenylalanine methyl ester, N-(tert-butoxycarbonyl)-4'-benzyloxybiphenyl alanine ethyl ester, N-(benzyloxycarbonyl)-4'-benzyloxybiphenylalanine methyl ester, N-(benzyloxycarbonyl)-4'-benzyloxybiphenylalanine ethyl ester, N-(tert-butoxycarbonyl)-2',4'-dimethoxybiphenylalanine methyl ester, N-(tert-butoxycarbonyl)-2',4'-dimethoxybiphenylalanine ethyl ester, N-(benzyloxycarbonyl)-2',4'-dimethoxybiphenylalanine methyl ester, N-(benzyloxycarbonyl)-2',4'-dimethoxybiphenylalanine ethyl ester, N-(tert-butoxycarbonyl)-3',4'-dimethoxybiphenylalanine methyl ester, N-(tert-butoxycarbonyl)-3',4'-dimethoxybiphenylalanine ethyl ester, N-(benzyloxycarbonyl)-3',4'-dimethoxybiphenylalanine methyl ester, N-(benzyloxycarbonyl)-3',4'-dimethoxybiphenylalanine ethyl ester, N-(tert-butoxycarbonyl)-2'-hydroxybiphenylalanine methyl ester, N-(tert-butoxycarbonyl)-2'-hydroxybiphenylalanine ethyl ester, N-(benzyloxycarbonyl)-2'-hydroxybiphenylalanine methyl ester, N-(benzyloxycarbonyl)-2'-hydroxybiphenylalanine ethyl ester, N-(tert-butoxycarbonyl)-3'-hydroxybiphenylalanine methyl ester, N-(tert-butoxycarbonyl)-3'-hydroxybiphenylalanine ethyl ester, N-(benzyloxycarbonyl)-3'-hydroxybiphenylalanine methyl ester, N-(benzyloxycarbonyl)-3'-hydroxybiphenylalanine ethyl ester, N-(tert-butoxycarbonyl)-4'-hydroxybiphenylalanine methyl ester, N-(tert-butoxycarbonyl)-4'-hydroxybiphenylalanine ethyl ester, N-(benzyloxycarbonyl)-4'-hydroxybiphenylalanine methyl ester, N-(benzyloxycarbonyl)-4'-hydroxybiphenylalanine ethyl ester, N-(tert-butoxycarbonyl)-3'-nitrobiphenylalanine methyl ester, N-(tert-butoxycarbonyl)-3'-nitrobiphenylalanine ethyl ester, N-(benzyloxycarbonyl)-3'-nitrobiphenylalanine methyl ester, N-(benzyloxycarbonyl)-3'-nitrobiphenylalanine ethyl ester, N-(tert-butoxycarbonyl)-4'-nitrobiphenylalanine methyl ester, N-(tert-butoxycarbonyl)-4'-nitrobiphenylalanine ethyl ester, N-(benzyloxycarbonyl)-4'-nitrobiphenylalanine methyl ester, N-(benzyloxycarbonyl)-4'-nitrobiphenylalanine ethyl ester, N-(tert-butoxycarbonyl)-2'-trifluoromethylbiphenylalanine methyl ester, N-(tert-butoxycarbonyl)-2'-trifluoromethylbiphenylalanine ethyl ester, N-(benzyloxycarbonyl)-2'-trifluoromethylbiphenylalanine methyl ester, N-(benzyloxycarbonyl)-2'-trifluoromethylbiphenylalanine ethyl ester, N-(tert-butoxycarbonyl)-3'-trifluoromethylbiphenylalanine methyl ester, N-(tert-butoxycarbonyl)-3'-trifluoromethylbiphenylalanine ethyl ester, N-(benzyloxycarbonyl)-3'-trifluoromethylbiphenylalanine methyl ester, N-(benzyloxycarbonyl)-3'-trifluoromethylbiphenylalanine ethyl ester, N-(tert-butoxycarbonyl)-4'-trifluoromethylbiphenylalanine methyl ester, N-(tert-butoxycarbonyl)-4'-trifluoromethylbiphenylalanine ethyl ester, N-(benzyloxycarbonyl)-4'-trifluoromethylbiphenylalanine methyl ester, N-(benzyloxycarbonyl)-4'-trifluoromethylbiphenylalanine ethyl ester, N-(tert-butoxycarbonyl)-3',5'-bis(trifluoromethyl)biphenylalanine methyl ester, N-(tert-butoxycarbonyl)-3',5'-bis(trifluoromethyl)biphenylalanine ethyl ester, N-(benzyloxycarbonyl)-3',5'-bis(trifluoromethyl)biphenylalanine methyl ester and N-(benzyloxycarbonyl)-3',5'-bis(trifluoromethyl)biphenylalanine ethyl ester.

In the present invention, the resulted biphenylalanine ester compound (1) is hydrolyzed using protease produced by a microorganism belonging to *Bacillus* sp. in the presence of at least one alkali selected from an alkali metal hydroxide and an alkaline earth metal hydroxide (the alkali may be simply called as caustic alkali below). When the compound is hydrolyzed using the protease, the L-form is predominantly hydrolyzed. This reaction can be carried out in the presence of a caustic alkali and an amino acid, and can be carried out in the presence of a caustic alkali and aminosulfonic acid.

As for the protease produced by a microorganism belonging to *Bacillus* sp., it is preferably to use protease produced by *Bacillus licheniformis* since it has excellent enantioselectively. Typical examples of the protease originated from *Bacillus licheniformis* include protease originated from *Bacillus licheniformis* containing subtilisin. Alkalase (produced by Novozymes Corporation) is preferable, and Alkalase 2.4 L (produced by Novozymes Corporation) is the most preferable.

A purity or form of the protease is not limited, and the protease can be used in various forms such as pure enzyme, crude enzyme, a microorganism-cultured material, microbial cells, or their treated material. Examples of the treated material include lyophilized microbial cells, a material of crushed microbial cells, and an extract of microbial cells. Further, for example, the enzyme having the above-described various purities or forms can be used by fixing on an inorganic carrier such as silica gel and ceramics, cellulose or ion-exchange resin.

The amount of the protease is not limited, but is usually 0.001 to 0.5 g, and preferably 0.001 to 0.1 g expressed in terms of pure enzyme based on 1 g of the biphenylalanine ester compound (1).

The compound is hydrolyzed with the protease while keeping pH of 6 to 13, preferably 6 to 10, and more preferably 6 to 9.5 although depending on a kind of protease. High optical purity can be obtained by hydrolyzing the compound within the above-described pH range.

Further, the hydrolysis is usually carried out in water or a mixed solvent of an organic solvent and water. However, the hydrolysis is preferably carried in the mixed solvent of an organic solvent and water since the high optical purity product is obtained in the solvent.

A method to make pH within the above-described range is, for example, a method of adding an aqueous caustic alkali solution, a buffer such as a phosphate buffer (for example, disodium hydrogenphosphate, sodium dihydrogenphosphate, dipotassium hydrogenphosphate, potassium dihydrogenphosphate) or an acetate buffer (for example, sodium acetate, potassium acetate), an aqueous caustic alkali solution in the presence of a buffer, an aqueous caustic alkali solution in the presence of an amino acid, or an aqueous caustic alkali solution in the presence of an aminosulfonic acid. An aqueous alkali solution and a buffer can be used as a solvent.

In the present invention, amino acid is an organic compound containing both of an amino group and a carboxyl group in one molecule. The organic compound includes imino acid in which a hydrogen atom of an amino group is changed into an annular structure together with a side chain portion. The amino group includes a substituted amino group or a substituted amino group having an annular structure. The amino acid does not only include α-amino acid but also β-amino acid, γ-amino acid, δ-amino acid and the like. Typical examples of the α-amino acid include neutral amino acids such as glycine, alanine, α-aminobutyric acid, leucine, isoleucine, valine, phenylalanine, tryptophan, thyrosin, methionine, cysteine, threonine, serine, proline, hydroxyproline, asparagine and glutamine; acidic amino acids such as aspartic acid and glutamic acid; and basic amino acids such as lysine, tryptophan, arginine, ornithine, histidine and hydroxylysine. Typical examples of the β-amino acid include β-alanine and β-aminobutyric acid. Typical examples of the γ-amino acid include γ-aminobutyric acid. Typical examples of the δ-amino acid include 5-aminovaleric acid.

In the present invention, aminosulfonic acid is an organic compound having a sulfo group instead of a carboxyl group in an amino acid. Typical examples include taurine, N-methyltaurine and 2-(4-morpholinyl)ethanesulfonic acid.

In the present invention, a method to have pH within the above-described range is a method using an aqueous caustic alkali solution from the viewpoints of economical efficiency and reducing of wastes which are not proper for environment. A method using an aqueous caustic alkali solution in the presence of an amino acid and a method using an aqueous caustic solution in the presence of an aminosulfonic acid are preferable. In addition, amino acid or aminosulfonic acid is used as a buffer.

In the above-described method, caustic alkali is at least one selected from an alkali metal hydroxide and an alkaline earth metal hydroxide. An alkali metal hydroxide is preferable, and potassium hydroxide and sodium hydroxide are more preferable as the caustic alkali. Further, the amino acid is preferably glycine and the aminosulfonic acid is preferably taurine.

A concentration of the aqueous caustic alkali solution is not limited, but is usually 2 to 30%, preferably 3 to 15%, and more preferably 3 to 13%. When the concentration of the aqueous alkali solution is within this range, a high optical purity material can be produced more easily.

In a case of using a buffer, the concentration of the buffer is usually 0.05 to 0.8M, preferably 0.1 to 0.8M, and more preferably 0.1 to 0.5M. When the concentration of the buffer is within this range, a high optical purity material can be produced. The amount of the buffer is usually 2 to 100 mL, and preferably 2 to 10 mL based on 1 g of the biphenylalanine ester compound (1) from the viewpoints of prevention to deposit salts, reaction control, and productivity, although depending on the concentration.

The amount of the aqueous caustic alkali solution is usually 0.45 to 0.7 equivalents, and preferably 0.48 to 0.65 equivalents, based on the biphenylalanine ester compound (1) from the viewpoints to keep a proper pH range, prevent to stop reaction, and prevent to naturally hydrolyze.

When amino acid or aminosulfonic acid is used, the amount of it is usually 0.05 to 1 mole, preferably 0.1 to 0.5 mole, and more preferably 0.1 to 0.3 mole based on 1 mole of the biphenylalanine ester compound (1). When the amount of amino acid or aminosulfonic acid is within this range, a pH range needed for an enzyme reaction can be easily kept, and the reaction can be smoothly advanced.

The organic solvent is a hydrophobic organic solvent or a hydrophilic organic solvent.

Examples of the hydrophobic organic solvent include ethers such as tert-butyl methyl ether and diisopropyl ether; and hydrocarbons such as toluene, hexane, cyclohexane and heptanes. Examples of the hydrophilic organic solvent include ethers such as tetrahydrofuran; alcohols such as methanol, ethanol, isopropanol, n-butanol and tert-butanol; sulfoxides such as dimethyl sulfoxide; ketones such as acetone; and nitrites such as acetonitrile. These organic solvents can be used solely or by mixing two or more kinds.

The organic solvent is preferably tert-butyl methyl ether and toluene. Tert-butyl methyl ether is the most preferable.

The amount of the organic solvent is usually 1 to 50 mL, preferably 1 to 5 mL, based on 1 g of the biphenylalanine ester compound (1) from the viewpoints of prevention to reduce a reaction rate due to deposition of raw materials and generated materials and economical efficiency.

The hydrolysis is carried out by mixing the biphenylalanine ester compound (1), a protease produced by a microorganism belonging to *Bacillus* sp., a caustic alkali, a solvent, and an amino acid or aminosulfonic acid if necessary.

The order of adding those is not limited. For example, an adding method is as follows.
(i) The biphenylalanine ester compound (1) dissolved with the organic solvent is added to the aqueous caustic alkali solution or the aqueous caustic solution/the buffer, and then the protease is added.
(ii) The aqueous caustic alkali solution or the aqueous caustic solution/the buffer are added to the biphenylalanine ester compound (1) dissolved with the organic solvent, and then the protease is added.
(iii) The protease is added (with water if necessary) to the biphenylalanine ester compound (1) dissolved with the organic solvent, and then the caustic alkali is added (preferably, dropped).
(iv) The protease and the amino acid or aminosulfonic acid are added (with water if necessary) to the biphenylalanine ester compound (1) dissolved with the organic solvent, and then the aqueous caustic alkali solution is added (preferably, dropped).

The protease can be added more during a reaction if necessary. Further, when pH of a reaction liquid is decreased during a reaction, it is preferable to keep the pH of the reaction liquid within the above-described range by using a proper pH adjustment agent.

The pH adjustment agent is a caustic alkali such as sodium hydroxide, potassium hydroxide, lithium hydroxide, calcium hydroxide, magnesium hydroxide, or barium hydroxide, or its aqueous solution.

The reaction temperature in hydrolysis is preferably 30 to 60° C., more preferably 35 to 55° C., and the most preferably 40 to 45° C. from the viewpoints of stability and a reaction rate of enzyme.

The reaction time for hydrolysis is usually 3 to 24 hours, and preferably 4 to 15 hours.

A salt of an optically active biphenylalanine compound (2) (L-form) generated by the hydrolysis can be separated from an unreacted optically active biphenylalanine compound (3) (D-form) by separating an aqueous layer from an organic layer of a reaction mixture after the reaction. At this time, the aqueous layer includes the salt of the optically active biphenyl lanine compound (2), and the organic layer includes the optically active biphenylalanine compound (3).

When a mixed solvent of a hydrophobic organic solvent and water is used in the hydrolysis, a resulted reaction mixture can be separated as it is.

When a hydrophobic organic solvent is not used in the hydrolysis or a mixture cannot be separated as it is since usage amounts of the hydrophobic organic solvent and/or water are small, the proper amounts of the hydrophobic organic solvent and/or water can be added and then separated.

Examples of the hydrophobic organic solvent include ethers such as tert-butyl methyl ether and diisopropyl ether, hydrocarbons such as toluene, hexane, cyclohexane and heptane; halogenated hydrocarbons such as dichloromethane, 1,2-dichloroethane, chloroform and chlorobenzene; and esters such as ethyl acetate, methyl acetate and butyl acetate.

In a liquid separation operation, pH of the water layer is ordinarily set to 6.5 to 12, and preferably 7.5 to 11.

The optically active biphenylalanine compound (2) or its salt can be obtained from the resulted water layer by the following methods.

1) A crude product of the salt of the optically active biphenylalanine compound (2) (an alkali metal hydroxide or an alkaline earth metal hydroxide) can be obtained by distilling off the solvent from the water layer.

2) The salt of the optically active biphenylalanine compound (2) can be isolated by adding an inorganic salt and an organic solvent to the water layer, extracting it, and distilling off the organic solvent.

Here, Examples of the inorganic salt include sodium chloride, potassium chloride and ammonium chloride. Potassium chloride and sodium chloride are preferable from the viewpoint of economical efficiency and solubility of the salt of the optically active biphenylalanine compound (2). The amount of the inorganic salt is preferably 30 to 100 g based on 100 g of the salt of the optically active biphenylalanine compound (2) included in the water layer from the viewpoints of the extraction rate.

Examples of the organic solvent include toluene, tert-butyl methyl ether and ethyl acetate. Toluene and tert-butyl methyl ether are preferable.

The amount of the organic solvent is usually 60 g to 130 g, and preferably 80 g to 120 g, based on 100 g of the salt of the optically active biphenylalanine compound (2) included in the water layer.

In addition, when extraction is insufficient, pH can be adjusted to be neutrality or weak acidity by adding an acid.

Extraction is carried out ordinarily at 10 to 50° C.

3) The optically active biphenylalanine compound (2) can be isolated by making the water layer to be acidic (pH is usually 1 to 7, and preferably 1 to 4), extracting with an organic solvent, and distilling off the organic solvent. The same organic solvent as that used in the above-described extraction can be used.

The resulted optically active biphenylalanine compound (2) or salt thereof can be purified by a general method such as recrystallization or column chromatography. In addition, the salt of the optically active biphenylalanine compound (2) can be converted to the optically active biphenylalanine compound (2) by an acid if necessary.

On the other hand, the optically active biphenylalanine compound (3) can be isolated by distilling off the solvent from the organic layer. Further, the optically active biphenylalanine compound (3) included in the water layer can be recovered by extracting the water layer, which is separated by the liquid separation operation, with an organic solvent. The pH of the water layer in the extraction operation is usually 6.5 to 12, and preferably 7.5 to 11. The same organic solvent as that described as the hydrophobic organic solvent can be used.

The resulted optically active biphenylalanine compound (3) or salt thereof can be purified by a general method such as recrystallization or column chromatography.

The isolated optically active biphenylalanine compound (3) is hydrolyzed according to an ordinary method so as to produce a compound in which $R^1$ is substituted by a hydrogen atom (an optical isomer (D-form) of the optically active biphenylalanine compound (2)) or salt thereof.

Further, the protective groups of the isolated optically active biphenylalanine compound (2) or salt thereof and the optically active biphenylalanine compound (3) are removed according to an ordinary method so that compounds in which $R^2$ is substituted by a hydrogen atom can be produced.

The optically active biphenylalanine compound (2) or salt thereof and the optically active biphenylalanine compound (3), which are produced by the method of the present invention, are useful as an intermediate to produce a medicament such as a neutral endopeptidase inhibitor. For example, according to a method described in JP-H06-228187A, an N-phosphonomethyl-biaryl-substituted dipeptide derivative described in the gazette can be produced by using the optically active biphenylalanine compound (2) or salt thereof and the optically active biphenylalanine compound (3).

When the optically active biphenylalanine compound (3) is a desired compound, the optically active biphenylalanine compound (2) or salt thereof is esterified so as to obtain the optically active biphenylalanine ester compound (2'), and then the compound (2') is racemized so as to be converted to the biphenylalanine compound (1). Thereby, the compound can be recycled for a raw material in the above-described hydrolysis reaction. The method is described as follows.

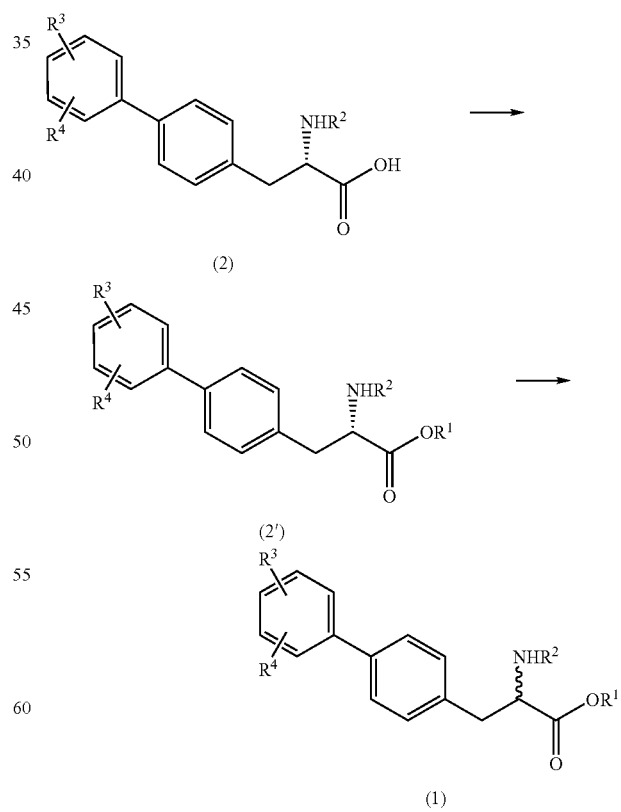

(where, $R^1$, $R^2$, $R^3$ and $R^4$ have the same meanings as described above.)

Esterifying

The optically active biphenylalanine ester compound (2') is produced by an esterification of the optically active biphenylalanine compound (2) or salt thereof.

In this esterification, a solution of an organic solvent of the optically active biphenylalanine compound (2) or salt thereof is used as it is by extraction after finishing the above-described hydrolysis, where the optically active biphenylalanine compound (2) or salt thereof is obtained by separating a mixture of the optically active biphenylalanine compound (2) or salt thereof and the optically active biphenylalanine compound (3).

The esterification can be carried out according to an ordinary method, and examples of the method include a method using an alcohol, such as methanol and ethanol, and an acid; a method using a sulfate, such as dimethyl sulfate and diethyl sulfate, and a base; a method using $R^1OH$ ($R^1$ has the same meaning as described above) and a condensing agent such as DCC (dicyclohexylcarbodiimide); and a method using alkyl halides, such as methyl iodide, bromoethane and benzyl chloride, and a base. Among these methods, the method using a sulfate and a base is preferable from the viewpoints of few by-products and simple procedures.

The method using a base and dimethyl sulfate will be described below.

Examples of the base include sodium hydrogencarbonate, potassium hydrogencarbonate, potassium carbonate, sodium hydroxide, potassium hydroxide, diisopropylethylamine, 2,6-dimethylpyridine, triethylamine and pyridine. Among those, sodium hydrogencarbonate is preferable.

The amount of the base is usually 0.3 to 1.2 moles based on 1 mole of the optically active biphenylalanine compound (2) or salt thereof in the solution.

The sulfate is preferably dimethyl sulfate from the viewpoints of reactivity and easy work-up.

The amount of the sulfate is usually 1.2 to 2.5 moles, and preferably 1.6 to 2.0 moles, based on 1 mole of the optically active biphenylalanine compound (2) or salt thereof in the solution.

As for a step of esterifying, a step for dropping sulfate to the solution including the base and the optically active biphenylalanine compound (2) or salt thereof is preferable from the viewpoints of reactivity.

The temperature of the esterification is usually 30 to 50° C. The reaction time is usually 1 to 10 hours although depending on the amount of the reagent or the reaction temperature. Finishing of the reaction can be confirmed by an HPLC analysis.

After the reaction is finished, an amine such as triethylamine is added, and the reaction liquid is stirred at 30 to 50° C. for 2 to 5 hours so as to decompose residual sulfate. The amount of the amine is approximately 10% by mole based on the used sulfate.

Then, the reaction liquid is separated, and a resulted organic layer is dehydrated. Dehydration can be carried out using dehydrating agents such as anhydrous magnesium sulfate, anhydrous sodium sulfate, and molecular sieves. However, a method for azeotropic dehydration of a solvent forming an azeotrope with water (for example, toluene) is preferable from the viewpoint of easy operation.

The amount of the solvent forming an azeotrope may be the amount capable of sufficiently dehydrating, but is usually 50 to 100% by weight based on the amount of the solution.

In the following racemization, the water amount in the solution of the optically active biphenylalanine ester compound (2') is preferably 500 ppm or less. Thus, it is preferable to carry out sufficient dehydration.

The resulted solution of the optically active biphenylalanine ester compound (2') can be used as it is in the following racemization. Or, the solution can be used after isolating the optically active biphenylalanine ester compound (2') by a general method.

The optically active biphenylalanine ester compound (2') includes the same compound as that described in the example of the biphenylalanine ester compound (1) except the steric configuration is specified in the formula (2').

Racemization

The optically active biphenylalanine ester compound (2') obtained by the esterification is racemized so as to be converted to the biphenylalanine compound (1).

Racemization is usually carried out by operating a base in a solvent.

As for a solvent, it is preferable to add alcohols such as methanol, ethanol and isopropanol, to the solution of the optically active biphenylalanine ester compound (2') obtained by esterifying from the viewpoints of acceleration of racemization.

The amount of the alcohol is usually 80 to 120% by weight based on the weight of the optically active biphenylalanine ester compound (2').

Examples of the base include alkali metal alcoholates such as sodium methoxide, sodium ethoxide and potassium tert-butoxide; and alkali metal hydroxides such as sodium hydride and potassium hydride. Among those, an alkali metal alcoholate is preferable from the viewpoint of handling property, and sodium methoxide is particularly preferable from the viewpoint of economical efficiency.

The amount of the base is 80 to 120% by mole based on the optically active biphenylalanine ester compound (2').

The temperature of the racemization is usually 30 to 50° C., and preferably 35 to 45° C. The reaction time is usually 10 minutes to 6 hours although depending on the using amount of the reagent and the reaction temperature. Finishing of the racemization reaction can be confirmed by HPLC.

After the racemization is finished, an acid such as acetic acid is preferably added to the reaction liquid so as to suppress decomposition of ester. In this case, the amount of the acid is usually 1.1 to 1.3 moles based on 1 mole of the base used for the racemization.

A post-treatment after finishing the racemization is carried out according to an ordinary method.

The solution of the resulted biphenylalanine ester compound (1) can be supplied as it is for the hydrolysis with enzyme, and this compound (1) can be concentrated, dissolved in the other organic solvent such as tert-butyl methyl ether, and supplied for the hydrolysis.

In addition, when the optically active biphenylalanine compound (2) or salt thereof is a desired compound, the optically active biphenylalanine ester compound (3) is racemized so as to be converted to the biphenylalanine compound (1). Thereby, the compound can be recycled in the above-described hydrolysis.

This racemization can be carried out by using a solution of an organic solvent of the optically active biphenylalanine ester compound (3), which is obtained by extraction after finishing the hydrolysis, and using the same method as that of the above-described racemizing method.

Then, the present invention is described in detail below with reference to examples, but the present invention is not limited to these examples.

In the following examples, a phosphate buffer having pH of 7.0 and a phosphate buffer having pH of 8.0 are adjusted in the following methods.

Phosphate Buffer Having pH of 7.0

An aqueous solution obtained by dissolving 17.25 g (0.099 mole) of dipotassium hydrogenphosphate with 900 mL of water, adjusting pH to be 7.0 with phosphoric acid, and adding water to have the total amount of 1 L.

Phosphate Buffer Having pH of 8.0

An aqueous solution obtained by dissolving 7.38 g (0.052 mole) of disodium hydrogenphosphate and 5.46 g (0.035 mole) of sodium dihydrogenphosphate dihydrate with 195 mL of water, and adjusting pH to be 8.0 with a 20% sodium hydroxide aqueous solution.

An optical purity (an enantiomer excess ratio) of an optically active substance is determined by high-performance liquid chromatography (HPLC).

HPLC Analyzing Conditions

Column; Chiral Pack AD-RH (Daicel Chemical Industries, Ltd.) (4.5 mmφ×15 cm, 5 μm)

Moving phase; Liquid A; 0.1% phosphate aqueous solution
　Liquid B; Acetonitrile

Separation conditions; Liquid B 40% (15 minutes)—30 minutes
　80% (0 minute) Gradient Column temperature; 40° C.

Flowing rate: 1.0 mL/minute

Detector: UV (254 nm)

Holding time; L-N-Boc-biphenylalanine; 10 minutes
　D-N-Boc-biphenylalanine; 13 minutes
　L-N-Boc-biphenylalanine methyl ester; 27 minutes
　D-N-Boc-biphenylalanine methyl ester; 30 minutes

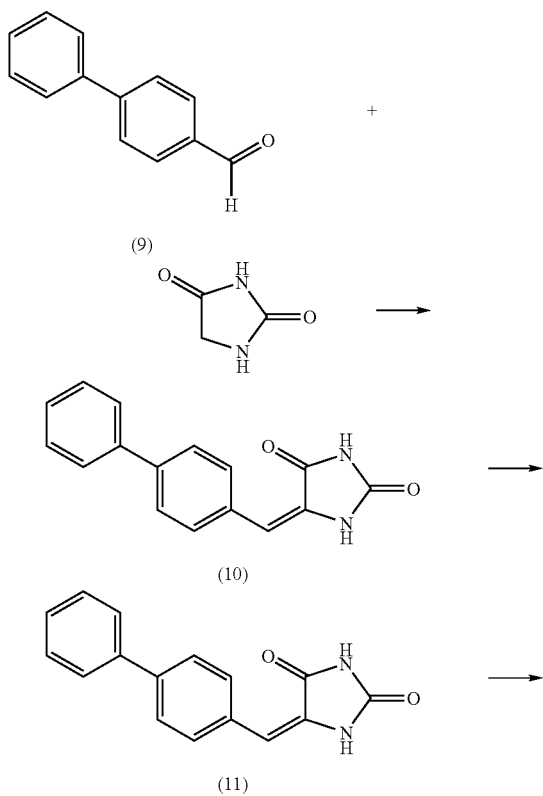

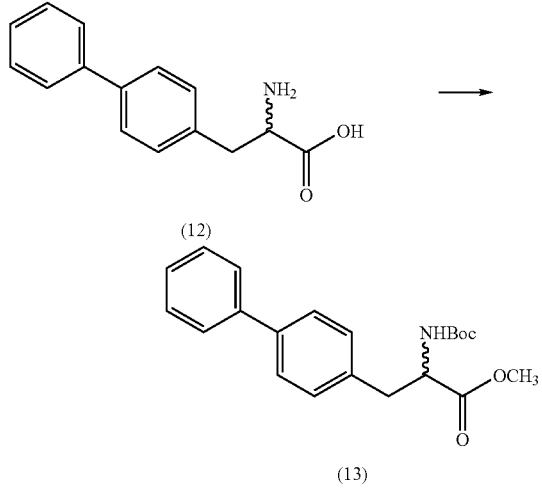

Production Example 1

DL-Biphenylalanine (12)

4-Biphenylaldehyde (9) (100.0 g, 0.549 mole), hydantoin (82.4 g, 0.823 mole) and ammonium acetate (63.5 g, 0.824 mole) were heated and refluxed for 5 hours in acetic acid (360 mL).

Then, a hydantoin compound (10) (143.14 g, yield of 98.7%) was obtained by adding water (360 mL) to the refluxed mixture, cooling to a room temperature, filtrating a crystal, and washing with isopropanol-water (1:1, 400 mL).

Then, a reduced compound (11) (60.63 g, yield of 100%) was obtained by adding 5% palladium-carbon (50% water content, 2.7 g) to a mixture of the hydantoin compound (10) (60.2 g), tetrahydrofuran (THF) (540 mL) and water (60 mL), stirring under a hydrogen atmosphere of 0.5 MPa and 60° C. for 3 hours, filtrating to remove a catalyst, and concentrating the filtrate.

Then, DL-biphenylalanine (12) (53.25 g, yield of 98.4%) was obtained by adding sodium hydroxide (36.65 g) to a mixture of the reduced compound (11) (59.7 g, 0.224 mole), ethylene glycol (300 mL), and water (10 mL), stirring at 130 to 140° C. for 5 hours, cooling to a room temperature, adding water (130 mL), adding an aqueous hydrochloric solution including concentrated hydrochloric acid (85 g) and water (99 g) so as to make pH of the mixture to be 6.9, filtrating the resulted crystal, washing the crystal with water (300 mL), washing with methanol (300 mL), and drying.

Production Example 2

D-N-Boc-biphenylalanine methyl ester (13)

DL-Biphenylalanine (12) (20.0 g, 0.0829 mole) was added to an aqueous solution of 10% sodium hydroxide (116 g, 0.29 mole) After THF (50 mL) was added to the mixture, a THF (20 mL) solution of di-tert-butyl dicarbonate (23.5 g, 0.108 mole) was dropped to the mixture at 30° C. over 1 hour. Further, tetrabutylammonium bromide (0.20 g, 0.62 mole) was added to the mixture, and then dimethyl sulfate (12.5 g, 0.099 mole) was dropped to the mixture. After the mixture was stirred at a room temperature for 16 hours, dimethyl sulfate (5.4 g, 0.0428 mole) was added to the mixture, and the mixture was stirred at 35° C. for 4.5 hours. Then, dimethyl sulfate (2.93 g, 0.0232 mole) was further added, and the mixture was stirred at 35° C. for 2.5 hours.

Then, 104.1 g of a tert-butyl methyl ether (MTBE) solution containing D-N-Boc-biphenylalanine methyl ester was obtained by adding MTBE (40 mL) and water (100 mL) to the mixture, and removing a water layer from the mixture by phase-separation.

When the solution was quantitative analyzed by HPLC, the content of D-N-Boc-biphenylalanine methyl ester was 29.4 g, and the yield from DL-biphenylalanine was 99.8%.

Then, D-N-Boc-biphenylalanine methyl ester (19.1 g) was obtained as a colorless crystal (recystallization yield of 86.6%) by concentrating and drying 78.1 g of the resulted MTBE solution of D-N-Boc-biphenylalanine methyl ester, and recrystallizing the resides from isopropanol (9 mL) and heptane (80 mL).

$^1$H-NMR (CDCl$_3$) δ; 1.42 (9H, s), 3.09 (1H, dd, J=5, 14 Hz), 3.16 (1H, dd, J=5, 14 Hz), 3.74 (3H, s), 4.55-4.70 (1H, m), 4.90-5.08 (1H, m), 7.20 (2H, d, J=8 Hz), 7.33 (1H, t, J=8 Hz), 7.43 (2H, t, J=8 Hz), 7.52 (2H, d, J=8 Hz), 7.57 (2H, d, J=8 Hz).

Example 1

Potassium Hydroxide Dropping Method

A reaction liquid was obtained by adding 99.49 g of water and 55.26 g of Alkalase 2.4 L FG (produced by *Bacillus licheniformis*) (Novozymes Corporation) to a solution in which 221.08 g (0.622 mole) of DL-N-Boc-biphenylalanine methyl ester was dissolved with 467.76 g of MTBE, stirring it at 40° C., and stirring it at 40° C. for 22 hours while dropping 369.8 g (0.317 mole) of an aqueous solution of 5% potassium hydroxide thereto. The pH of the reaction liquid at this time was within the range of 6.82 to 9.58.

When the reaction liquid was analyzed, an optical purity of D-N-Boc-biphenylalanine methyl ester was 99.2% ee.

Example 2

Taurine Adding Method

A reaction liquid was obtained by adding 11.25 g of water, 1.76 g (14.1 mmoles) of taurine, and 4.50 g of Alkalase 2.4 L FG (produced by *Bacillus licheniformis*) (Novozymes Corporation) to a solution in which 25.0 g (70.3 mmoles) of DL-N-Boc-biphenylalanine methyl ester was dissolved with 41.14 g of MTBE, stirring it at 40° C., and stirring it at 40° C. for 17 hours while dropping 47.28 g (40.67 mmoles) of an aqueous solution of 5% potassium hydroxide thereto. The pH of the reaction liquid at this time was within the range of 6.30 to 8.16.

When the reaction liquid was analyzed, an optical purity of D-N-Boc-biphenylalanine methyl ester was 99.9% ee and an optical purity of L-N-Boc-biphenylalanine was 99.9% ee.

After allowing the reaction liquid to stand for 5 minutes, the reaction liquid was separated so as to obtain 35.72 g of an organic layer A and 83.46 g of a water layer A. Toluene (37.5 g) was added to the water layer A and stirred at 40° C. for 30 minutes. After allowing the mixed liquid to stand for 5 minutes, the liquid was separated so as to obtain 42.80 g of an organic layer B and 76.80 g of a water layer B. The organic layer A and the organic layer B were made to be together one, added with 58 g of water and 1.49 g of sodium carbonate, and stirred at 40° C. for 30 minutes. After allowing it to stand for 5 minutes, the liquid was separated so as to obtain 76.07 g of an organic layer C. The obtained organic layer C (76.07 g) was concentrated while keeping a temperature of 50° C. so as to distill off 63.2 g of the organic layer C.

Seventy-five (75) mL of methanol was added to 12.87 g of the concentrated residue, and 18.75 g of water was added to it while keeping a temperature of 40° C. A seed crystal of D-N-Boc-biphenylalanine methyl ester (2 mg) was added to the mixture, and stirred at 40° C. for 30 minutes. Twelve and a half (12.5) g of water was dropped to it over 30 minutes, and the mixture was kept at a temperature of 40° C. for 1 hour. Then, the mixture was cooled until 20° C. and filtrated. The obtained crystal was washed with a mixed solution of 8.75 g of methanol and 3.75 g of water.

A white crystal of D-N-Boc-biphenylalanine methyl ester (10.94 g) was obtained by drying the crystal under a reduced pressure. The yield of the D-N-Boc-biphenylalanine methyl ester was 43.8% based on DL-N-Boc-biphenylalanine methyl ester.

Example 3

Glycine Adding Method

A reaction liquid was obtained by adding 2.88 g of water, 0.27 g (3.6 mmoles) of glycine, and 1.53 g of Alkalase 2.4 L FG (produced by *Bacillus licheniformis*) (Novozymes Corporation) to a solution in which 6.38 g (18.0 mmoles) of DL-N-Boc-biphenylalanine methyl ester is dissolved with 10.50 g of MTBE, stirring it at 40° C., and stirring it at 40° C. for 18 hours while dropping 11.0 g (9.90 mmoles) of an aqueous solution of 5% potassium hydroxide thereto. The pH of the reaction liquid at this time was within the range of 6.53 to 8.90.

When the reaction liquid was analyzed, an optical purity of D-N-Boc-biphenylalanine methyl ester was 99.5% ee, and an optical purity of L-N-Boc-biphenylalanine methyl ester was 99.4% ee.

Example 4

Recycling of L Form after an Enzyme Hydrolysis (i) Methylation of L-N-Boc-Biphenylalanine A reaction liquid was obtained by adding 50 g of toluene and 37.5 g of sodium chloride to 328.54 g of an aqueous solution containing L-N-Boc-biphenylalanine potassium salt corresponding to L-N-Boc-biphenylalanine of 50.0 g (0.146 mole), where this solution was obtained by the similar method to that of Example 2 (Taurine adding method), stirring the mixture at 40° C. for 20 minutes, allowing the liquid to stand for 5 minutes, separating the liquid so as to obtain 156.23 g of an organic layer, adding 12.27 g (0.146 mole) of sodium hydrogencarbonate to the organic layer, stirring it at 40° C., dropping 33.15 g (0.263 mole) of dimethyl sulfate to the mixture over 2 hours, and stirring it at 40° C. for 1 hour. When the reaction liquid was analyzed, the residual L-N-Boc-biphenylalanine was a detection limit or less by an LC analysis.

Triethylamine (2.95 g, 0.029 mole) was added to the reaction liquid, and stirred at 40° C. for 3 hours. After allowing it to stand for 5 minutes, the liquid was separated so as to obtain 114.04 g of an organic layer. Toluene (86.72 g) was added to the organic layer, and concentrated while keeping a temperature of 50° C., and 57.92 g of the organic layer was distilled off. Then, 7.39 g of toluene was added to the residual liquid so as to obtain 150.23 g of a toluene solution. When the obtained toluene solution was quantitative analyzed, the yield of L-N-Boc-biphenylalanine methyl ester was 96.2% based on L-N-

Boc-biphenylalanine. Further, when the solution was measured by a Karl Fischer aquametry apparatus, the water content of the obtained toluene solution was 204 ppm.

(ii) Racemizing of L-N-Boc-Biphenylalanine Methyl Ester

A reaction liquid was obtained by adding 50 g of methanol to 150.23 g of a toluene solution containing 50 g (0.141 mole) of L-N-Boc-biphenylalanine methyl ester, stirring it at 40° C., dropping 27.20 g (0.141 mole) of a methanol solution of 28% sodium methylate to the toluene solution over 1 hour, and stirring it at 40° C. for 1 hour.

When the reaction liquid was analyzed, an optical purity of L-N-Boc-biphenylalanine methyl ester was 0.02% ee, and an LC side 100 value of L-N-Boc-biphenylalanine methyl ester was 89.3%.

Acetic acid (10.16 g, 0.169 mole) was dropped to the reaction liquid for 15 minutes, and stirred at 40° C. for 30 minutes.

Then, 50 g of water was added to the liquid, and stirred at 40° C. for 5 minutes. After allowing it to stand for 5 minutes, the liquid was separated so as to obtain 151.90 g of an organic layer. Forty-five (45) g of water and 2.37 g (0.028 mole) of sodium hydrogencarbonate were added to the organic layer, and stirred at 40° C. for 50 minutes. After allowing it to stand or 5 minutes, the liquid was separated so as to obtain 147.67 g of an organic layer. When the obtained solution was quantitative analyzed by LC, the yield of DL-N-Boc-biphenylalanine methyl ester was 89.7% based on L-N-Boc-biphenylalanine methyl ester.

The obtained solution was concentrated while keeping 54 to 56° C. so as to distill off 62.67 g of the solution. MTBE (75 g) was added to the residual solution and concentrated the solution so as to distill off 74.23 g of the solution. Then, 75 g of MTBE was added to the residual solution and concentrated the solution so as to distill off 84.71 g of the solution. Further, 51.46 g of MTBE was added to the residual solution to obtain 127.52 g of the solution. When the obtained solution was quantitative analyzed by LC, the yield of DL-N-Boc-biphenylalanine methyl ester was 89.5% based on the L-N-Boc-biphenylalanine methyl ester. Further, the toluene content in the MTBE solution was 18.5%.

(iii) Producing of D-N-Boc-Biphenylalanine Methyl Ester

When the above-obtained MTBE solution was hydrolyzed with enzyme by the similar conditions to those in Example 2 (Taurine adding method), an optical purity of D-N-Boc-biphenylalanine methyl ester in the reaction liquid was 99.4%, and an optical purity of L-N-Boc-biphenylalanine methyl ester was 100%.

LC analysis (HPLC) in methylation and recemization was carried out under the following conditions.

HPLC Analysis Conditions
Column; SUMIPAX A212 ODS (Sumika Chemical Analysis Service, Ltd.) (φ; 6 mm×L:15 cm)
Moving phase; Liquid A; 25 mM dipotassium hydrogenphosphate aqueous solution (pH was adjusted to be 6.8 with phosphoric acid)
Liquid B; Acetonitrile
Separation conditions; Liquid B 40% (5 minutes)-20 minutes-80% (5 minutes) Gradient
Column temperature; 40° C.
Flowing rate; 1.0 mL/minute
Detector; UV (254 nm)
Holding time; L-N-Boc-biphenyl alanine; 7 minutes
L-N-Boc-biphenyl alanine methyl ester; 24 minutes Reference Example 1

A solution in which 118 mg (0.33 mole) of DL-N-Boc-biphenylalanine methyl ester was dissolved with 2 mL of MTBE was added to 10 mL of a 0.1M phosphate buffer which had pH of 7.0. Four-tenth (0.4) mL of Alkalase 2.4 L FG (produced by *Bacillus licheniformis*) (Novozymes Corporation) was added to the solution, and stirred at pH of 6.82 to 7.0 and 40° C. for 8.5 hours.

When the reaction liquid was analyzed, an optical purity of D-N-Boc-biphenylalanine methyl ester was 99.7% ee, and an optical purity of L-N-Boc-biphenylalanine was 100% ee.

Reference Example 2

A solution in which 0.59 g (1.66 moles) of DL-N-Boc-biphenylalanine methyl ester was dissolved with 2 mL of MTBE was added to 5 mL of a 0.4M phosphate buffer which had pH of 7.0. 2 mL of Alkalase 2.4 L FG (Novozymes Corporation) was added to the solution, and stirred at pH of 6.57 to 7.0 and 40° C. for 7.5 hours.

When the reaction liquid was analyzed, an optical purity of D-N-Boc-biphenylalanine methyl ester was 96.7% ee, and an optical purity of L-N-Boc-biphenylalanine was 100% ee.

Reference Example 3

A solution in which 0.59 g (1.66 moles) of DL-N-Boc-biphenylalanine methyl ester was dissolved with 2 mL of MTBE was added to 5 mL of a 0.4M phosphate buffer which had pH of 8.0. Two (2) mL of Alkalase 2.4 L FG (Novozymes Corporation) was added to the solution, and stirred at 40° C. for 7.5 hours. At this time, pH of a water layer was 6.78. Then, the pH of the water layer was adjusted to be 8.1 with a 20% sodium hydroxide solution, and further stirred at 40° C. for 4 hours.

When the reaction liquid was analyzed, an optical purity of D-N-Boc-biphenylalanine methyl ester was 99.8% ee, and an optical purity of L-N-Boc-biphenylalanine was 100% ee.

Reference Example 4

A solution in which 3.7 mL of water and 0.59 g (1.66 moles) of DL-N-Boc-biphenylalanine methyl ester was dissolved with 2 mL of MTBE was added to 1.3 mL of a 0.4M phosphate buffer which had pH of 8.0. Two (2) mL of Alkalase 2.4 L FG (Novozymes Corporation) was added to the solution, and stirred at 40° C. for 7.5 hours. At this time, pH of a water layer was 6.50. Then, the pH of the water layer was adjusted to be 8.0 with a 20% sodium hydroxide solution, and further stirred at 40° C. for 4 hours.

When the reaction liquid was analyzed, an optical purity of D-N-Boc-biphenylalanine methyl ester was 99.5% ee, and an optical purity of L-N-Boc-biphenylalanine was 100% ee.

Reference Example 5

A solution in which 0.59 g (1.66 moles) of DL-N-Boc-biphenylalanine methyl ester was dissolved with 2 mL of MTBE was added to 5 mL of a 0.4M phosphate buffer which had pH of 8.0. One milliliter (1 mL) of Alkalase 2.4 L FG (Novozymes Corporation) was added to the solution and stirred at 40° C. for 2.5 hours. At this time, pH of a water layer was 6.85. Then, the pH of the water layer was adjusted to be 8.03 with a 20% sodium hydroxide solution and further stirred at 40° C. for 2.5 hours.

When the reaction liquid was analyzed, an optical purity of D-N-Boc-biphenylalanine methyl ester was 99.9% ee, and an optical purity of L-N-Boc-biphenylalanine was 100% ee.

Reference Example 6

A solution in which 0.59 g (1.66 moles) of DL-N-Boc-biphenylalanine methyl ester was dissolved with 2 mL of MTBE was added to 5 mL of a 0.4M phosphate buffer which had pH of 8.0. Three-fiftieth (0.06) mL of Alkalase 2.4 L FG (Novozymes Corporation) was added to the solution and stirred at 40° C. for 2.5 hours. At this time, pH of a water layer was 6.90. Then, the pH of the water layer was adjusted to be 8.0 with a 20% sodium hydroxide solution and further stirred at 40° C. for 2.5 hours.

When the reaction liquid was analyzed, an optical purity of D-N-Boc-biphenylalanine methyl ester was 99.8% ee and an optical purity of L-N-Boc-biphenylalanine was 100% ee.

Reference Example 7

A solution in which 1.0 g (2.81 moles) of DL-N-Boc-biphenylalanine methyl ester was dissolved with 2 mL of toluene was added to 8.5 mL of a 0.4M phosphate buffer which had pH of 8.0. One-tenth (0.1) mL of Alkalase 2.4 L FG (Novozymes Corporation) was added to the solution and stirred at 40° C. for 3 hours. At this time, pH of a water layer was 7.43. Then, the pH of the water layer was adjusted to be 8.1 with a 20% sodium hydroxide solution and further stirred at 40° C. for 3.5 hours. At this time, pH of a water layer was 7.18. Then, the pH of the water layer was adjusted to be 8.0 with an aqueous solution of 20% sodium hydroxide and further stirred at 40° C. for 3 hours.

When the reaction liquid was analyzed, an optical purity of D-N-Boc-biphenylalanine methyl ester was 96.9% ee and an optical purity of L-N-Boc-biphenylalanine was 100% ee.

Reference Example 8

Two and a half (2.5) g (0.0176 mole) of disodium hydrogenphosphate and 1.8 g (0.0115 mole) of sodium dihydrogenphosphate dihydrate were dissolved with 65 mL of water, and 1.86 ml of an aqueous solution of 20% sodium hydroxide was added to the solution so as to adjust pH to be 8.12.

A MTBE solution (45.4 g) of DL-N-Boc-biphenylalanine methyl ester [containing 16.6 g (0.0457 mole) of DL-N-Boc-biphenylalanine methyl ester] was added to the solution. Then, 2.5 mL of Alkalase 2.4 L FG (Novozymes Corporation) was added to the solution and stirred at 40° C. for 10 hours while keeping pH of a water layer at 7.44 to 8.45 with an aqueous solution 20% sodium hydroxide.

Then, the reaction liquid was separated and the obtained water layer was extracted by 30 ml of toluene. A toluene solution (69.29 g) of D-N-Boc-biphenylalanine methyl ester was obtained by combining the organic layers and washing the solution with an aqueous solution of 3% sodium carbonate.

When the solution was analyzed with HPLC, the content of D-N-Boc-biphenylalanine methyl ester was 8.36 g, and an optical purity was 99.9% ee. The yield from DL-N-Boc-biphenylalanine methyl ester was 50%.

The content of L-N-Boc-biphenylalanine in the water layer was 7.57 g, and an optical purity was 100% ee. The yield from DL-N-Boc-biphenylalanine methyl ester was 47.5%.

D-N-Boc-biphenylalanine methyl ester $^1$H-NMR (CDCl$_3$) δ; 1.42 (9H, s), 3.09 (1H, dd, J=5, 14 Hz), 3.16 (1H, dd, J=5, 14 Hz), 3.74 (3H, s), 4.55-4.70 (1H, m), 4.90-5.08 (1H, m), 7.20 (2H, d, J=8 Hz), 7.33 (1H, t, J=8 Hz), 7.43 (2H, t, J=8 Hz), 7.52 (2H, d, J=8 Hz), 7.57 (2H, d, J=8 Hz).

L-N-Boc-biphenylalanine $^1$H-NMR (CDCl$_3$) δ; 1.48 (9H, s), 3.12 (1H, dd, J=5, 14 Hz), 3.24 (1H, dd, J=5, 14 Hz), 4.55-4.70 (1H, m), 4.90-4.99 (1H, m), 7.26 (2H, d, J=8 Hz), 7.33 (1H, t, J=8 Hz), 7.42 (2H, t, J=8 Hz), 7.53 (2H, d, J=8 Hz), 7.56 (2H, d, J=8 Hz).

In each example, absolute configurations of D-form and L-form were determined by comparing the holding times with a standard product in HPLC using the above-described chiral column.

The production method of the present invention can produce a compound having an optically active biphenylalanine structure from low cost raw materials, with high optical purity and an easy operation, without giving much load to environment. Therefore, the production method is very advantageous industrially.

The invention claimed is:

1. A method for producing an optically active biphenylalanine compound of the formula (2):

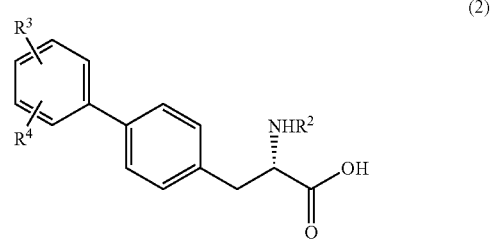

(2)

wherein, R$^2$ is a protective group of an amino group, and R$^3$ and R$^4$ are each independently a hydrogen atom, a halogen atom, an alkyl group, a haloalkyl group, a hydroxyl group, an alkoxy group, a cyano group, or a nitro group or a salt thereof and an optically active biphenylalanine ester compound of the formula (3):

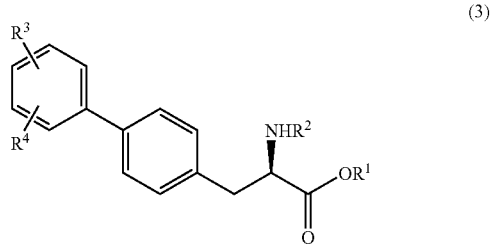

(3)

wherein, R$^1$ is an alkyl group, a haloalkyl group, an alkenyl group, a cycloalkyl group, an aryl group being optionally substituted, or an aralkyl group being optionally substituted; and R$^2$, R$^3$ and R$^4$ have the same meanings as described above which comprises the step of hydrolyzing a biphenylalanine ester compound of the formula (1):

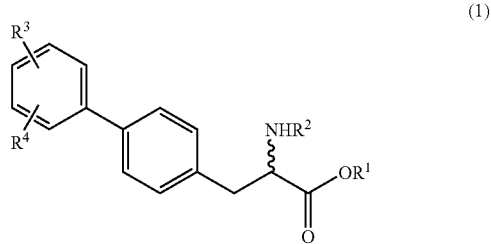

(1)

wherein, $R^1$, $R^2$, $R^3$ and $R^4$ have the same meanings as described above
with protease produced by a microorganism belonging to *Bacillus* sp. in the presence of at least one alkali selected from an alkali metal hydroxide and an alkaline earth metal hydroxide.

2. The method according to claim 1, wherein the hydrolysis is carried out in the presence of an amino acid and at least one alkali selected from an alkali metal hydroxide and an alkaline earth metal hydroxide.

3. The method according to claim 1, wherein the hydrolysis is carried out in the presence of an aminosulfonic acid and at least one alkali selected from an alkali metal hydroxide and an alkaline earth metal hydroxide.

4. The method according to claim 1, wherein the method further comprises the step of separating the optically active biphenylalanine compound of the formula (2) or its salt and the optically active biphenylalanine ester compound of the formula (3) after the hydrolysis.

5. The method according to claim 1, wherein the alkali is an alkali metal hydroxide.

6. The method according to claim 2, wherein the amino acid is glycine.

7. The method according to claim 3, wherein the aminosulfonic acid is taurine.

8. The method according to claim 2, wherein the alkali is an alkali metal hydroxide.

9. The method according to claim 6, wherein the alkali is an alkali metal hydroxide.

10. The method according to claim 3, wherein the alkali is an alkali metal hydroxide.

11. The method according to claim 7, wherein the alkali is an alkali metal hydroxide.

12. The method according to claim 1, wherein the protease is produced by *Bacillus licheniformis*.

13. The method according to claim 1, wherein $R^1$ is an alkyl group.

14. The method according to claim 13, wherein $R^1$ is a methyl group or an ethyl group.

15. The method according to claim 1, wherein $R^2$ is tert-butoxycarbonyl group.

16. The method according to claim 1, wherein $R^3$ and $R^4$ are hydrogen atoms.

17. The method according to claim 1, wherein the hydrolysis is carried out while keeping the pH range of 6 to 13.

18. The method according to claim 1, wherein the hydrolysis is carried out while keeping the pH range of 6 to 10.

19. The method according to claim 1, wherein the hydrolysis is carried out in a mixed solvent of an organic solvent and water.

20. The method according to claim 19, wherein the organic solvent is at least one selected from tert-butyl methyl ether and toluene.

21. The method according to claim 20, wherein the organic solvent is tert-butyl methyl ether.

22. The method according to claim 1, wherein the hydrolysis is carried out at 30 to 60° C.

23. The method according to claim 1, wherein the hydrolysis is carried out at 35 to 55° C.

* * * * *